(12) United States Patent
Jackson (10) Patent No.: US 9,999,755 B2
(45) Date of Patent: Jun. 19, 2018

(54) CONFORMABLE TISSUE EXPANDER (71) Applicant: OXTEX LIMITED, Oxford (GB)

(72) Inventor: David Edward Jackson, Wallingford (GB)

(73) Assignee: OXTEX LIMITED, Oxford (GB)

( * ) Notice: Subject to any disclaimer, the term of this patent is extended or adjusted under 35 U.S.C. 154(b) by 197 days.

(21) Appl. No.: 14/912,277

(22) PCT Filed: Aug. 13, 2014

(86) PCT No.: PCT/GB2014/052484
§ 371 (c)(1),
(2) Date: Feb. 16, 2016

(87) PCT Pub. No.: WO2015/022535
PCT Pub. Date: Feb. 19, 2015

(65) Prior Publication Data
US 2016/0199628 A1 Jul. 14, 2016

(30) Foreign Application Priority Data
Aug. 16, 2013 (GB) .................... 1314708.7

(51) Int. Cl.
A61M 29/00 (2006.01)
A61F 2/00 (2006.01)
(Continued)

(52) U.S. Cl.
CPC ............. A61M 29/00 (2013.01); A61B 90/02 (2016.02); A61F 2/0059 (2013.01); A61L 31/10 (2013.01);
(Continued)

(58) Field of Classification Search
CPC .................. A61M 29/02; A61M 29/00; A61M 2202/0007; A61F 2/0059;
(Continued)

(56) References Cited

U.S. PATENT DOCUMENTS 4,615,704 A * 10/1986 Frisch .................... A61B 90/02
128/899
5,005,591 A 4/1991 Austad
(Continued)

FOREIGN PATENT DOCUMENTS

CN 102639163 A 8/2012
EP 2470233 7/2012
(Continued)

OTHER PUBLICATIONS

First Office Action and Search Report issued by the State Intellectual Property Office of the People's Republic of China in connection with Chinese Application No. 201480045453.4 dated Apr. 27, 2017.
(Continued)

Primary Examiner — Katrina Stransky
(74) Attorney, Agent, or Firm — Meunier Carlin & Curfman LLC (57) ABSTRACT The present invention provides a tissue expander (10) comprising a self-inflating core (12) having a non-inflated state and an inflated state and a coating (14) surrounding said core (12), wherein said core (12) comprises two or more segments (16) of dried compacted material of height H joined to each other by conformable linking portions (18) of height h where H is greater than h. the conformable linking portions (18) allow for the expander (10) to be conformed to a desired profile either before or after insertion under the skin of a patient.

32 Claims, 4 Drawing Sheets (51) Int. Cl.
*A61L 31/10* (2006.01)
*A61L 31/14* (2006.01)
*A61B 90/00* (2016.01)

(52) U.S. Cl.
CPC ........... *A61L 31/145* (2013.01); *A61L 31/146* (2013.01); *A61F 2210/0061* (2013.01); *A61F 2250/0004* (2013.01); *A61M 2202/0007* (2013.01)

(58) Field of Classification Search
CPC ..... A61F 2210/0061; A61F 2250/0004; A61L 31/10; A61L 31/145; A61L 31/146; A61B 2017/00526; A61B 2017/00792; A61B 2017/00898; A61B 2017/00942; A61B 90/02; A61B 90/00; A61B 19/24
See application file for complete search history.

(56) References Cited

U.S. PATENT DOCUMENTS

| | | | |
|---|---|---|---|
| 5,192,326 A | 3/1993 | Bao et al. | |
| 5,496,368 A | 3/1996 | Wiese | |
| 6,228,116 B1* | 5/2001 | Ledergerber | A61F 2/0077 623/8 |
| 2002/0091443 A1 | 7/2002 | Yoon | |
| 2006/0155163 A1* | 7/2006 | Yachia | A61B 5/205 600/29 |
| 2008/0306505 A1* | 12/2008 | Manders | A61M 29/00 606/192 |
| 2010/0114312 A1* | 5/2010 | Glicksman | A61F 2/12 623/11.11 |
| 2011/0077682 A1* | 3/2011 | Gregory | A61F 13/00008 606/213 |
| 2011/0112383 A1 | 5/2011 | Voss et al. | |
| 2012/0265165 A1* | 10/2012 | Bucknall | A61L 27/26 604/500 |
| 2014/0142523 A1* | 5/2014 | Steinbaugh | A61F 13/00008 604/304 |
| 2015/0351900 A1* | 12/2015 | Glicksman | A61F 2/12 623/8 |
| 2017/0035999 A1* | 2/2017 | Wijay | A61M 29/02 |
| 2017/0259049 A1* | 9/2017 | Gregory | A61F 13/00008 |

FOREIGN PATENT DOCUMENTS

| | | |
|---|---|---|
| GB | 2139898 A | 11/1984 |
| WO | 2011051731 A2 | 5/2011 |

OTHER PUBLICATIONS

International Search Report and Written Opinion of the International Searching Authority from PCT Application No. PCT/GB2014/052484, dated Oct. 31, 2014, 9 pages.
Search Report of the GB Intellectual Property Office from Application No. GB1314708.7, dated Feb. 12, 2014, 4 pages.
Examination Report of the GB Intellectual Property Office from Application No. GB1314708.7, dated Oct. 5, 2015, 2 pages.
International Preliminary Report on Patentability issued by the International Bureau of WIPO from PCT Application No. PCT/GB2014/052484 dated Feb. 16, 2016, 6 pages.
Second Office Action issued by the State Intellectual Property Office of the People's Republic of China in connection with Chinese Application No. 201480045453.4 dated Jan. 4, 2018.

* cited by examiner

CONFORMABLE TISSUE EXPANDER

The present invention relates to expandable components and relates particularly but not exclusively to components known as tissue expanders. Such expanders are used by medical, veterinary and dental staff to cause the expansion of patient tissue in advance of corrective or supplemental surgery and generally are such as to have a controlled rate of expansion and may also be configured to have a delayed expansion capability. A particular aspect of the present invention is directed to providing an arrangement which is more easily configured to accommodate complex shapes.

Tissue expanders are now a key component in reconstructive plastic surgery and are used for example in the treatment of congenital abnormalities and acquired defects.

One known form of tissue expander is described in EP10776126 and from which it will be appreciated that they generally comprise a dried then compressed material which, when re-hydrated will expand to re-gain any height lost during compression. The rate of expansion may be controlled by coating the expandable material in a bio-degradable coating which, upon insertion in the patient, will degrade upon exposure to moisture and then allow the moisture to access the expandable de-hydrated material such as to hydrate it and cause it to expand. An alternative approach is to make the expandable material as an Interpenetrating Network of bio-degradable material and expandable material which, in combination, provide the delay and the expansion. The expandable material can be formed from a number of materials but new forms of hydrogel (a gel in which water is the dispersion medium) are of particular use in such applications. Such expanders are generally known as "self-inflating tissue expanders".

Whilst the above-mentioned arrangement is able to offer control over the delay and the rate of expansion they are generally of a standard size and are not easily modified prior to insertion such as to accommodate differing patient specific requirements. Such requirements may include contouring of the shape such as to accommodate a closer fit with underlying bone or tissue structure and/or altering the shape of the expander such as to accommodate physical restrictions in the specific application.

It is an object of the present invention to provide a tissue expander which improves on those already known and may able to offer at least some degree of pre and post insertion modification such as to accommodate the requirements listed above.

Accordingly, according to a first aspect of the present invention, there is provided a tissue expander comprising a self-inflating core having a non-inflated state and an inflated state and a coating surrounding said core, wherein said core comprises two or more segments of dried compacted material of height H joined to each other by conformable linking portions of height h where H is greater than h.

Preferably, said core comprises upper and lower surfaces and said linking portions are formed as depressions in each of said surfaces.

Said core may comprise a strip of segments separated by linking portions or may comprise comprises a two dimensional array of segments linked by linking portions.

In one arrangement said linking portions comprise depressions of depth D and width W and wherein said width W decreases as said depth D increases.

Preferably, said conformable linking portions comprise compression moulded compacted material and are contiguous with said two or more segments.

Preferably the arrangement includes two or more conformable linking portions and wherein said two or more conformable linking portions extend substantially perpendicular to each other.

In one arrangement there are provided two or more conformable linking portions and said two or more conformable linking portions extend at an obtuse or acute angle to each other.

Preferably, said coating comprises a moulded coating surrounding said core and is moulded thereonto.

Advantageously, said coating includes an outer surface for exposure to moisture and an inner surface in intimate contact with the core and one or more apertures extending from said outer surface to said inner surface such as to allow for the passage of moisture to said core.

Advantageously, the arrangement further including one or more porous plugs within one or more of said one or more apertures.

Advantageously, said one or more porous plugs comprise a porous polymer.

Preferably, said segments each include upper and lower surfaces and one or more of said one or more apertures are provide at positions which terminate on one or other of said upper or lower surfaces.

Preferably, said self-inflating core comprises a hydrogel.

Preferably, said coating comprises a water impermeable coating.

Advantageously, said coating comprises a flexible expandable material.

In one arrangement said self-inflating core comprises a dried and compacted material.

In a preferred arrangement said self-inflating core comprises a compacted material having a central portion of compacted material having a first higher hardness/density HD and a peripheral portion of compacted material having a second lower hardness/density LD less than said first higher density HD, a border between said central portion and said peripheral portion and wherein said coating includes a plurality of first apertures through said coating at positions displaced from said border.

The tissue expander may comprise a regular two dimensional array or an irregular shaped two dimensional array.

In one arrangement said segments are each of different pre compacted height.

The present invention will now be more particularly described by way of example only with reference to the accompanying drawings, in which.

The present invention may employ a self-inflating polymer gel. The self-inflating polymer network of the present invention may be based on a hydrophilic polymer network which is capable of absorbing water without dissolution. The hydrophilic properties are provided by functional groups on the polymer(s) (e.g. hydroxyl, carboxyl or amide functional groups). Preferably the self-inflating polymer network comprises at least one monomer containing —COOH, >C=O, —OH, or —NH2 groups. The resistance to dissolution is a result of the presence of structural cross-linkages, crystalline regions or entanglements. Such materials are typically termed "hydrogels". The hydrogel contains two components, namely the polymer network (i.e. the gel), which is constant in quantity, and a variable aqueous component. In the anhydrous state (prior to implantation), the material is normally referred to as a xerogel. The anhydrous material is hygroscopic and absorbs/adsorbs water from its local environment to hydrate the network. The self-inflating polymer network may swell to many times its dry mass. Typically, the aqueous phase comprises 90% or more, preferably 95% or more of the total mass of the self-inflating polymer network at equilibrium. The expansion of the self-inflating polymer network is driven by the diffusion of water molecules into the polymer network which is due to osmosis and the interaction between the polymer and water molecules in order to reduce the Gibbs free energy of the system when the polymer is introduced into an aqueous environment, i.e. from tissue fluid in vivo. The self-inflating polymer network approaches its equilibrium state when the driving force for the mixing between the polymer species and the solvent is balanced by the restoring force of the chains in the network due to the elasticity of polymer network. Whilst there are number of self-inflating polymers that could be used hydrogels are the most suited to medical applications. It is preferable that the hydrogel comprises functional groups on the polymer (e.g. hydroxyl, carboxyl or amide functional groups or others which provide the hydrophilic properties thereof. The expansion of the above self-inflating polymer is driven by the diffusion of water molecules into the polymer network which is due to osmosis and the interaction between the polymer and water molecules in order to reduce the Gibbs free energy of the system when the polymer is introduced into an aqueous environment, such as may be experienced when inserted within a human or animal body. The self-inflating polymer network approaches its equilibrium state when the driving forces for the mixing between any polymer species and any solvent is balanced by the restoring force of the chains in the network due to the elasticity of the polymer network itself.

Figure 1:
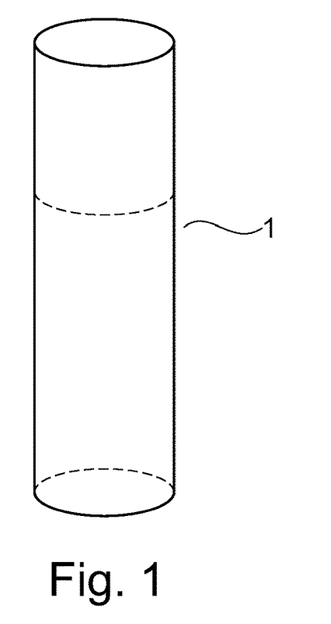
FIG. 1 is a diagrammatic representation of a rod of preformed expandable material.
Figure 2:
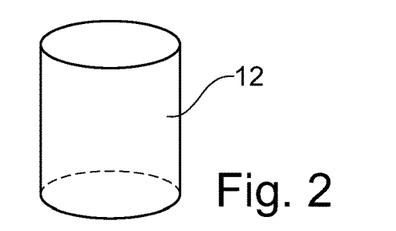
FIG. 2 is a view of a short length of the material shown in FIG. 1 prior to a drying step.
Figure 3:
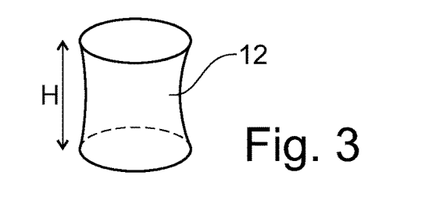
FIG. 3 is a view of the material of FIG. 2 after a drying or de-hydration step has been performed thereon.

A first manufacturing process which may be employed in the manufacture of the present product is illustrated in FIGS. 1 to 3, in which a partially hydrated self-inflating polymer gel is formed into a pre-determined shape 1, a portion of which 1a is cut therefrom to form the shorter portion 12 or core shown first in FIG. 2. The Height H of the core 12 of FIG. 2 is selected to be sufficient to provide the height $H^4$ required in a finished expander after expansion has taken place. It will, therefore, be appreciated that height H may be varied to suit different requirements. The self-inflating polymer is hydrophilic and, therefore, able to absorb water without dissolution and it is this property that is employed to advantage in the present invention.

Whilst there are number of self-inflating polymers that could be used hydrogels are the most suited to medical applications. It is preferable that the hydrogel comprises functional groups on the polymer (e.g. hydroxyl, carboxyl or amide functional groups or others which provide the hydrophilic properties thereof.

The expansion of the above self-inflating polymer is driven by the diffusion of water molecules into the polymer network which is due to osmosis and the interaction between the polymer and water molecules in order to reduce the Gibbs free energy of the system when the polymer is introduced into an aqueous environment, such as may be experienced when inserted within a human or animal body. The self-inflating polymer network approaches its equilibrium state when the driving forces for the mixing between any polymer species and any solvent is balanced by the restoring force of the chains in the network due to the elasticity of the polymer network itself.

Figure 6:
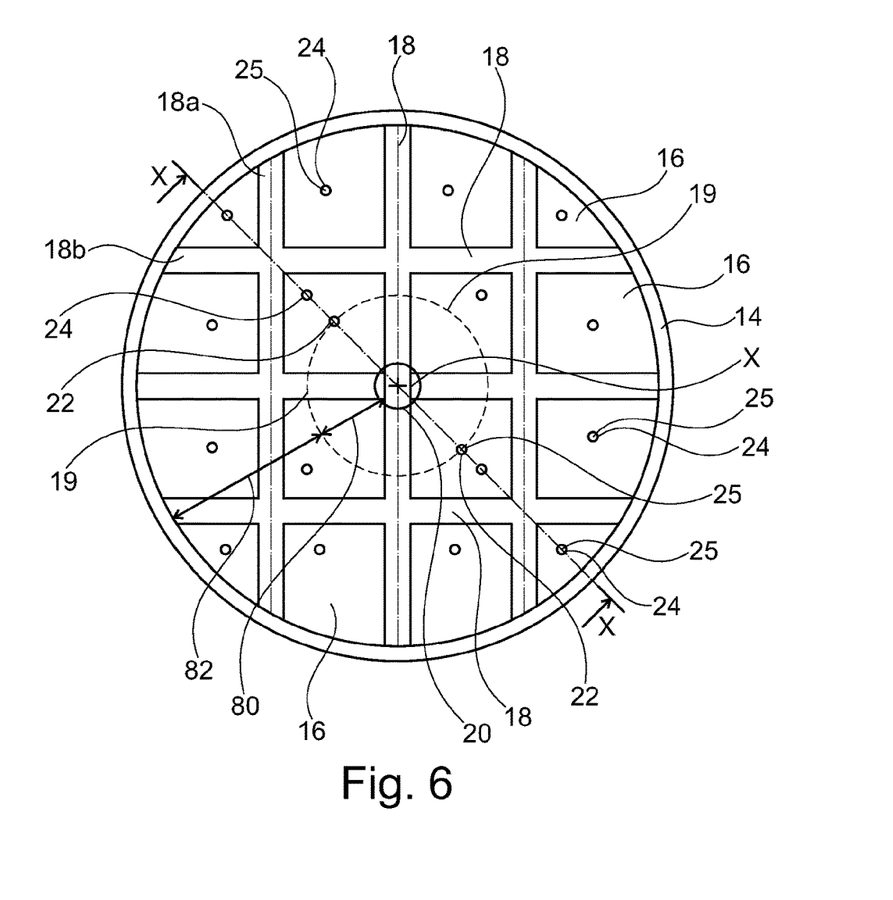
FIG. 6 is a plan view of a first form of compacted material as shown in FIG. 1.
Figure 7:
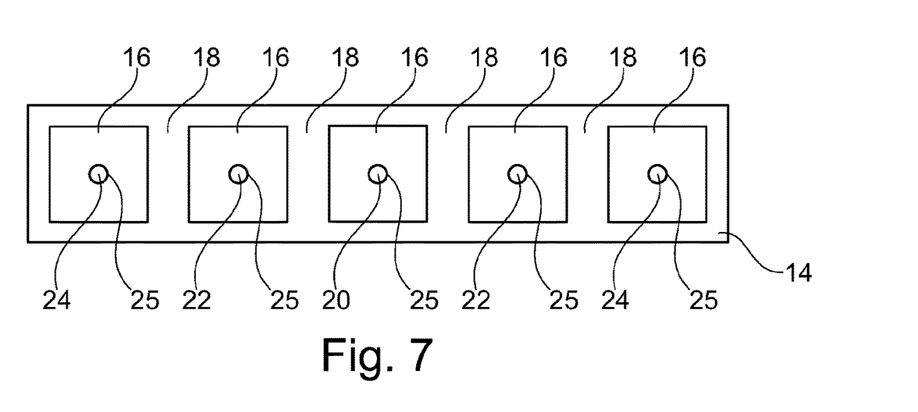
FIGS. 7 and 8 are plan and cross-sectional views of a preferred arrangement of expandable implant.
Figure 8:
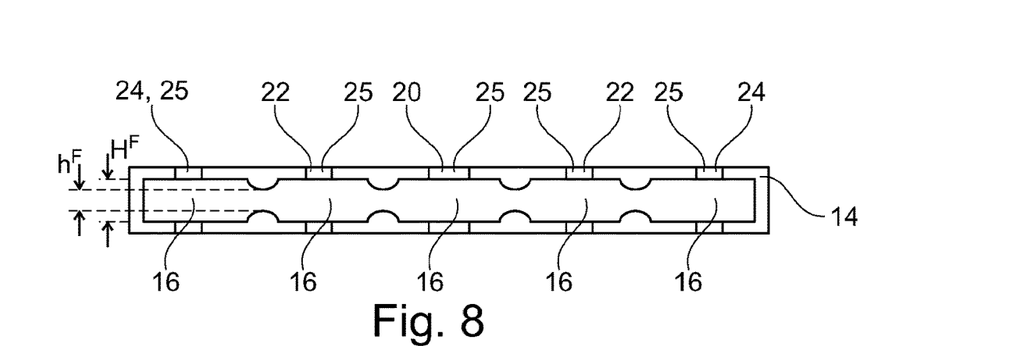

The core 12 of FIG. 2 is then dried such as to remove the pre-hydration moisture therefrom and produce the component of FIG. 3 which is in the state required for compression forming into the shaped core 12 shown more specifically in FIGS. 6 to 8. It will be appreciated that the partial pre-hydration step will make it easier to cut into a desired shape but that this step may be eliminated if the machinery is available to simply cut the de-hydrated starting material 1 to the desired length. This would also allow for the elimination of the de-hydration step between FIGS. 2 and 3.

Figure 4:
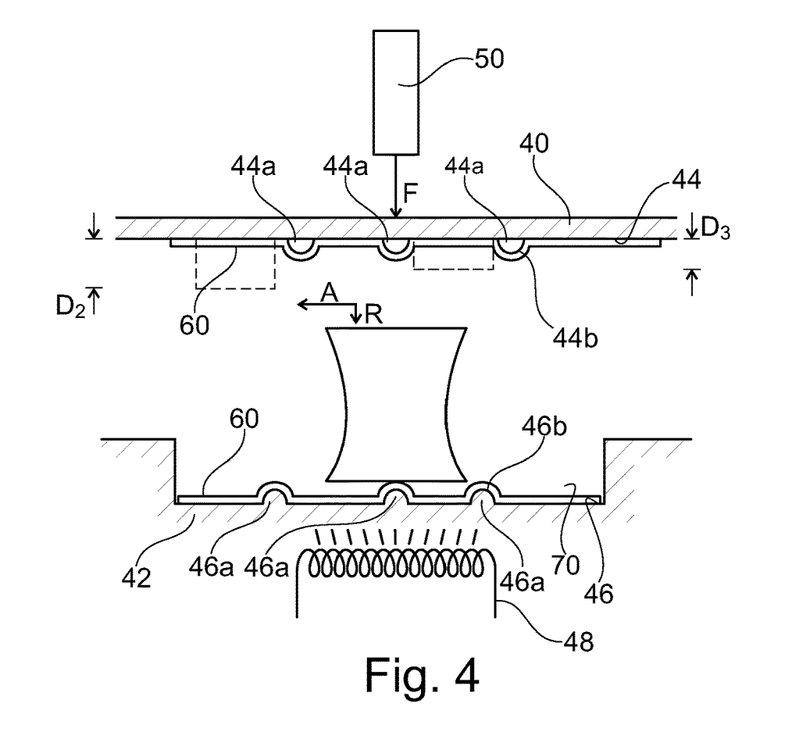
FIG. 4 is a diagrammatic representation of a compaction apparatus and illustrates the shape of the material of FIG. 3 both before and after compaction.

Compression of the core 12 is illustrated diagrammatically in FIG. 4 and from which it will be appreciated that the dried un-compressed core 12 is placed between two compression members 40, 42 having confronting surfaces 44, 46 which, in operation, contact the core 12. One or both surfaces 44, 46 is further provided with a series of protrusions 44a, 46a which extend from the surface 40 such as, in operation, to penetrate into the core 12 during compression and form areas of reduced height h, as will be discussed in more detail below. Preferably, the protrusions are provided with tapered end portions 44b, 46b such as to form a tapered indent 60 into the compressed core 12 the function of which will be described in detail later herein. A heater and compression ram, shown schematically at 48, 50 respectively are used to heat and compress the core as detailed below. Compression is done by applying heat and pressure to the core (typically applied in one direction or plane so as to reduce the height H) to provide a subsequent anisotropic expansion principally in the direction of compression. The combination of heat at around or above the glass transition temperature (Tg) of the polymer and pressure causes the molecular chains to realign. Clearly heating should be lower than the degradation temperature of the polymer.

Figure 5:
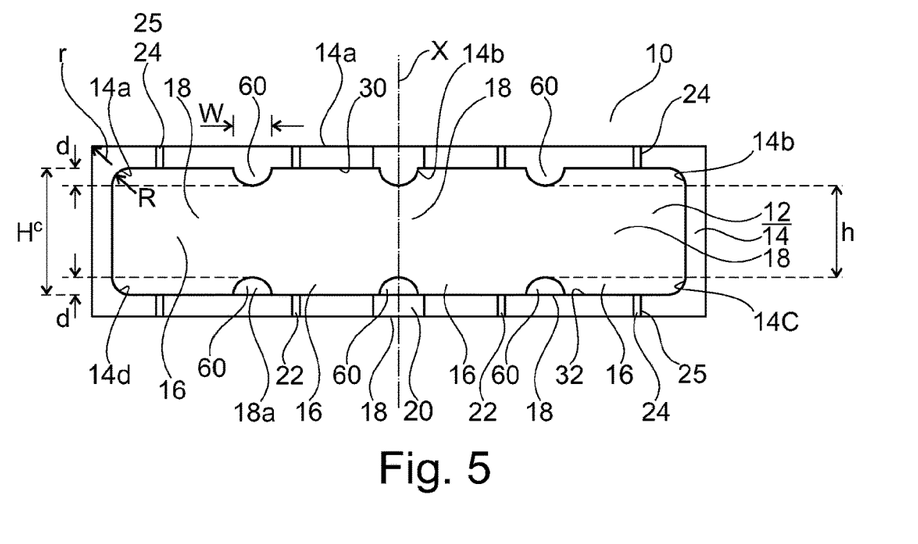
FIG. 5 is a diagrammatic cross-sectional view of pre-formed expandable material.

The compression step reduces the height H of the core whilst increasing the width W, as shown in FIG. 5. Segments 16 of height $H^C$ are divided from each other by thinner linking portions 18 of height h formed by protrusions 40b, as discussed above. The loss in height $(H-H^C)$ corresponds to the increase in height H when the core is re-hydrated in use and, hence, the starting height H of the pre-compressed core 12 and the compressed height $H^C$ may be adjusted as required in order to ensure the desired expansion is achieved. Indeed, the degree of compression of each segment may be individually determined by altering the depth D2, D3 of the mould portion associated with the segment in particular such as to compress segments by different amounts. During expansion the width W will decrease whilst the height H will increase. The compression step itself places the core 12 under a number of forces which include both axial and radial forces shown schematically by arrows A and R. the axial force A is that which is applied to reduce the height H and is directly related to the degree of compression but the radial force R has a component which depends on the frictional properties at the junction of the core material and the confronting surfaces 44, 46. In essence, the greater the degree of friction (µF) the greater the element of radial force R required to compress the core 12.

An interlayer in the form of a thin sheet of material 60 may be placed on one or other or both surfaces 44, 46 prior to compaction. Alternatively, the surfaces 44, 46 may be coated with said sheet material. The sheet 60 effectively acts as a friction reducing layer as direct contact between the compaction tools surfaces 44, 46 and the core 12 is avoided. Materials such as PTFE, silicone, aluminium foil etc. may be employed and each will provide a different effect during the compression step. It has been found that a core compacted as described above will have an inner region 80 having a first higher average density/hardness and a second outer or peripheral portion 82 having a second lower (average) density/hardness and a border 19 between said regions which defines a region at which expansion after hydration is initiated.

It will be appreciated that compression of the core 12 will generally cause the core 12 to expand evenly in all radial directions such as to form a generally circular arrangement as shown in FIG. 6. However, it is possible to create a more regular arrangement, such as is shown in FIGS. 7 to 10 by providing a recess 70 in one of surfaces 44, 46 which, in operation, acts to confine the expansion of the core 12 during compression. The recess 70 may be regularly or irregularly shaped if so desired.

Reference is now made to FIGS. 5 to 10 which illustrate the finished product in more detail and from which it will be appreciated that the segmented arrangement formed by the process of FIG. 4 is then provided with an outer coating 14 having a thickness T which is applied in order to provide a barrier to water impregnation. Such a layer 14 is required to be flexible and able to accommodate expansion of the core 12 as and when required whilst also being water impermeable other than through apertures discussed later herein. The layer may comprise silicone as this will expand with the core 12 but other materials such as polyurethane, polypropylene, rubber etc. may also be used. In essence, the coating 14 must resist the passage of water therethrough but be sufficiently flexible as to accommodate the subsequent change in shape and dimension of the core as it expands. One or more of first, second and third apertures 20, 22, 24 are provided in the coating such as to extend through the coating 14 and to one or other or both of the upper and lower surfaces 30, 32 of the core itself. The apertures 20, 22, 24 provide a route through which water can reach the core 12 and may be plugged with a semi-permeable barrier material 25 so as to control the rate of water ingress. The properties of the semi-permeable barrier material 25 may be varied between finished articles such as to provide a more tailored product where the rate of fluid absorption can be pre-defined or they may be set as a constant between finished products if so desired. The expansion of the core 12 initiates at the barrier 19 and, thus, one can vary the delay between insertion and expansion by varying the distance ZA, ZB of any apertures 20, 22 from the border 19. In operation, water will take some time to penetrate through the apertures and then track towards the border 19 and, hence, the greater the distances ZA, ZB the greater the delay in expansion. Clearly, apertures can be placed in association with the central region and/or the peripheral region and may even be placed immediately above the border 19 if it is desired to have zero delay in expansion. The size and/or number of the holes may be altered so as to increase or decrease the rate of expansion once it has been initiated. In the example shown, aperture 20 is radially inward of border 19, aperture 22 is positioned on border 19 whilst aperture 24 is positioned radially outwardly of border 19.

From the above, it will be appreciated that the present invention is able to take control over the delay before expansion and the rate of expansion once initiated by varying the position, number and size of the holes and the permeability of the holes 20, 22, 24 by the provision of plugs 25 of defined permeability or the elimination thereof as desired. Further, the surgeon may be able to modify the final produce before insertion by simply filling in holes 20, 22, 24 or removing already inserted plugs 25 such as to alter the rate of expansion. Still further, the surgeon may be able to increase the number of holes and/or the position of added holes should that be desired. It will also be appreciated that the coating 14 is in intimate contact with the core 12 which ensures that any fluid which is passed through to the core is channelled in a controlled manner to the border region 19 such as to ensure consistency in the delay before expansion takes place.

FIG. 5 provides a cross-sectional view of the tissue expander 10 of FIG. 6 and illustrates a plurality of holes 20, 22, 24 in fluid communication with both the upper and lower surfaces 30, 32 of the core itself. The provision of holes on both sides, whilst not being essential, will help ensure the expansion takes place evenly on both sides and may also ensure a more rapid and complete expansion. The holes 20, 22, 24 may be evenly or unevenly spaced and may be positioned in circumferentially spaced manner around a central axis X if the core. In certain arrangements a central hole 23 may be provided on the axis X which may be used individually or in combination with other holes 20, 22, 24. FIG. 5 also illustrates in detail the joining portion 18 between each segment 16 which form depressions of depth D and width W. preferably, the width W decreases as the depth D increases such as to form a tapered portion over at least the end thereof towards a tip 18a. The joining portions form a continuous joint with the segments 16 and are contiguous therewith. The thinning of the core 12 at the joining portions 18 allows for the flexing of the implant 10 along the joint which will allow a surgeon to contour the implant 10 to a desired shape prior to or potentially even after insertion into a patient.

FIG. 5 also illustrates the detail associated with the corners of the expander 10 and from which it will be appreciated that the compression of the core 12 will create a lozenge shaped component having corners 14a, 14b, 14c, 14d with a radius of curvature R. it has been found that the coating 14 when applied by dip coating techniques can be thinner at the corners than might be desirable and premature rupturing of the coating 14 can occur at these positions. In order to solve this problem, the present invention also proposes an arrangement in which the coating is applied such as to have a thicker coating thickness T at the corners. Such an arrangement can be achieved by injection moulding the coating in a mould containing the compressed core 12 in a mould which has a defined shape with corners adjacent the corners 12a-12d of the core which are of a lesser radius r than radius R. the mould radius r will then translate into a coating radius r at the corners 14a-14d which is less than the radius R, thus creating an increased local thickness T at the corners. This extra thickness at the crucial corner positions will ensure that premature rupturing during expansion is substantially eliminated. The reader will appreciate that the coating is applied in a manner which will space fill the recesses formed at the joining portions 18 but as the coating is formed from flexible material this will not adversely affect the ability to contour the shape of the finished implant 10.

Figure 9:
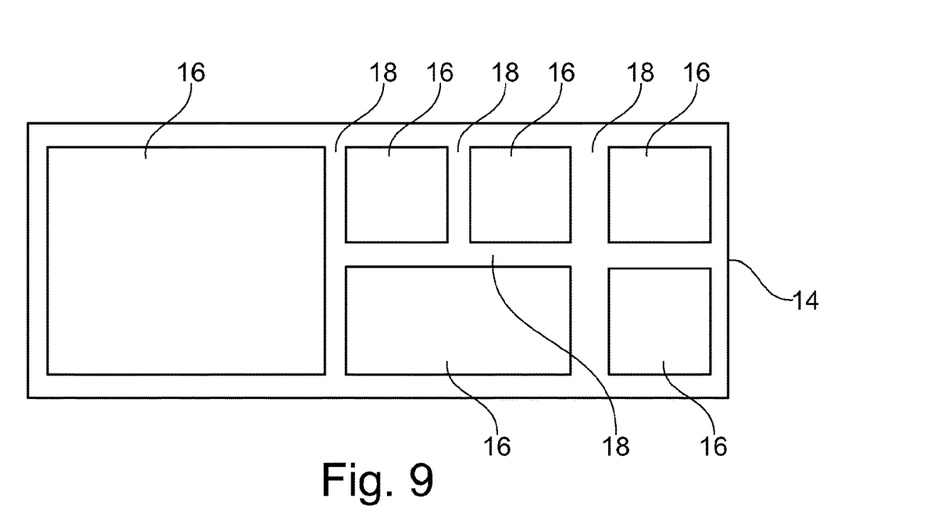
FIGS. 9 and 10 are plan views of alternative forms of the implant of FIG. 1.
Figure 10:
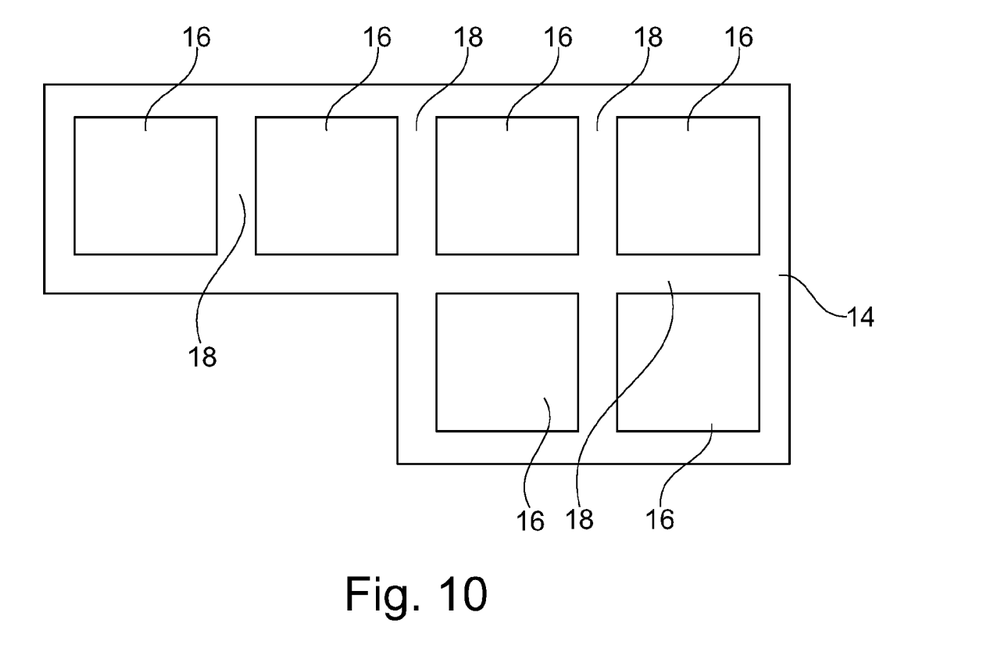

Referring now more particularly to FIGS. 7 to 10, it will be appreciated that the implant 10 may be formed with one or more segments 16 positioned as a two dimensional array or regular or irregular shape. FIGS. 7 and 8 illustrate one preferred arrangement in which a row of segments 16 are provided with joining portions 18 therebetween. FIG. 9 illustrates a generally regular rectangular arrangement having segments 16 of different shapes and sizes. FIG. 10 illustrates an irregular shaped two dimensional array having one side with more segments 16 than the other. The reader will appreciate that many other arrangements will present themselves and that arrangements may be selected depending upon the particular use that the implant is to be put to. Each of FIGS. 7 to 10 share a common feature in the form of linking portions 18 which are contiguous with the segments and may extend in directions substantially perpendicular to each other or at an acute or obtuse angle relative to each other (not shown). The linking portions 18 effectively divide the segments 16 and are provided to allow for flexing of the implant 10 either before or after insertion. The linking portions 18 being much thinner are much more flexible and, in effect, provide a flexure point or line L about which the segments 16 can pivot or bend such as to allow them to be appropriately positioned relative to each other.

The present invention also provides a method of manufacturing a tissue expander 10, as described above, including the steps of first selecting a hydrated self-inflating hydrophilic core material and then forming said selected material to a given height H and width W by, for example, cutting from a length thereof. The cut length is then dried to remove as much moisture as possible which will cause the material to shrink in height H and width W which is required prior to the next step which is compaction. The core 12 is then compacted between, for example, the compression members 40, 42 of FIG. 4 one or both of which is provided with protrusions 44a, 46a which, in operation, are pressed into the core material 12 such as to produce the linking portions 18, as discussed above. The process is such as to reduce the height H thereof whilst increasing the width W such as to produce a compacted core 12 into one or other of the shapes shown in FIGS. 6 to 10. The compression step also impresses protrusions 44a, 46a into the core material such as to form linking portions 18 of reduced height h adjacent to and linking with one or more of a plurality of segments 16 of greater height H which are formed therebetween. The depth D2, D3 of the tool at portions associated with segments in the finished core 12 may be altered or varied such as to impart a greater or lesser degree of compression of individual segments in the finished core 12. By virtue of the compaction process the compressed core 12 will have an inner region defined by the extent of arrow 80 of a first, higher, (average) density D and a peripheral region defined by the extent of arrow 82 of a second, lower, (average) density d, a border (19) between said central region (16) and said peripheral region (18).

The compaction process itself is controllable in as much as the rate of compaction, the temperature and the degree of friction can be controlled. Compression rates will depend on the materials being used and the temperature of compaction. The degree of friction between the compressing core 12 and the compression members 40, 42 is also important and can be controlled by the application of an interlayer 60 such as, for example, PTFE, silicone, aluminium foil etc. The interlayer 60 reduce the slipping friction μF which is present when the core is squashed radially outwardly and alteration of the friction will affect the profile of the slope of the densities and/or hardness discussed above. It will, therefore, be appreciated that one may alter the point at which the slipping friction and sticking friction profiles cross each other and, as this crossing point defines the barrier 19, it is possible to define the position of the border 19 in any formed core This is important as being able to define the position of the border 19 allows one to alter the position of the expansion initiation point as such takes place from the barrier portion 19 itself. Also, being able to control the position of the border portion 19 and ensure it is at a set position will allow one to accurately position any apertures 20, 22, 24 relative thereto such as to accurately set the delay before expansion takes place.

The next step comprises coating the core 12 with a protective coating designed to control ingress of water into the core 12. Whilst a number of coatings 14 can be used, it has been found that a Silicone layer lends itself to the present application as it has a good degree of flexibility, accommodates the desired expansion of the core 12 and is able to accommodate the formation of apertures 20, 22, 24 as and where desired. Whilst the coating 14 may be applied by dip coating, the present applicants have realised that dip coating often results in a thinning of the coating at the edges 12a-12d of the core which can be undesirable as the coating can rupture during expansion which will result in water penetration in an uncontrolled manner and more rapid and uncontrolled expansion of the core 12 than may be desired. In order to overcome this problem, the present invention including the step of forming the core material 12 with edges having a radius of curvature R and coating said coating 14 onto the core 12 by moulding said coating 14 around the core 12 and forming the coating material 14 with edges 14e adjacent the edges 12e of the core and having a radii of curvature r which is less than the radii of curvature R of the edges of the core 12. This step provides a thicker coating at the critical corner portions.

The coating 14 may be provided as a water impermeable coating and a plurality of apertures 20, 22, 24 may be provided through said coating 14 such as to allow for the passage of water into the core in a manner controlled by the position and size of the apertures. The apertures 20, 22 may also be provided with a plug 25 of semi-permeable material as discussed in detail above in relation to the apparatus portion of this application.

The implant 10 as described above is implanted under the tissue of a patient and the shape thereof may be adjusted by flexing the implant at the joining portions 18 which are thinner and more flexible than the segments 16. Water will pass through the apertures and expose the core 12 to moisture at a rate determined by the size, number and position of the apertures as may be modified by the material properties of any plug that may be inserted therein. Once water reaches the core 12 it will cause expansion thereof as the core adsorbs the water. This expansion will create a swelling pressure provided by the hydration of the polymer network (e.g. xerogel) to form a fully swollen polymer network (e.g. a hydrogel) which occurs in vivo. The self-inflating polymer network is preferably a xerogel/hydrogel, i.e. the network changes from a xerogel to a hydrogel as it absorbs water in vivo. The self-inflating polymer network may generate a swelling stress of up to 200 kPa and preferably at least 30 kPa.

The invention claimed is:

1. A tissue expander comprising a self-inflating core having a non-inflated state and an inflated state and a coating surrounding said core, characterized in that said core comprises two or more segments of dried compacted material of height H joined to each other by two or more conformable linking portions of height h where H is greater than h, and wherein said two or more conformable linking portions extend substantially perpendicular to each other.

2. The tissue expander of claim 1, wherein said core comprises upper and lower surfaces and wherein said linking portions are formed as depressions in each of said surfaces.

3. The tissue expander of claim 2, characterized in that said core comprises a regular two dimensional array of segments.

4. The tissue expander of claim 2, characterized in that said core comprises an irregular shaped two dimensional array of segments.

5. The tissue expander of claim 1, characterized in that said core comprises a two dimensional array of segments.

6. The tissue expander of claim 1, characterized in that said linking portions comprise depressions of depth D and width W and wherein said width W decreases as said depth D increases.

7. The tissue expander of claim 1, characterized in that said conformable linking portions comprise compression molded compacted material and are contiguous with said two or more segments.

8. The tissue expander of claim 1, characterized in that said coating comprises a molded coating surrounding said core and molded thereonto.

9. The tissue expander of claim 1, characterized in that said coating includes an outer surface for exposure to moisture and an inner surface in intimate contact with the core and one or more apertures extending from said outer surface to said inner surface such as to allow for the passage of moisture to said core.

10. The tissue expander of claim 9, characterized by further including one or more porous plugs within one or more of said one or more apertures.

11. The tissue expander of claim 9, characterized in that said one or more porous plugs comprise a porous polymer.

12. The tissue expander of claim 9, characterized in that said segments each include upper and lower surfaces and one or more of said one or more apertures are provided at positions which terminate on one or other of said upper or lower surfaces.

13. The tissue expander of claim 1, characterized in that said self-inflating core comprises a hydrogel.

14. The tissue expander of claim 1, characterized in that said coating comprises a water impermeable coating.

15. The tissue expander of claim 14, characterized in that said self-inflating core comprises a compacted material having a central portion of the compacted material having a first higher density HD and a peripheral portion of the compacted material having a second lower density LD less than said first higher density HD, a border between said central portion and said peripheral portion and wherein said coating includes a plurality of first apertures through said coating at positions displaced from said border.

16. The tissue expander of claim 1 characterized in that said segments are each of a different pre-compacted height.

17. A tissue expander comprising a self-inflating core having a non-inflated state and an inflated state and a coating surrounding said core, characterized in that said core comprises two or more segments of dried compacted material of height H joined to each other by two or more conformable linking portions of height h where H is greater than h, and wherein said two or more conformable linking portions extend at an obtuse or acute angle to each other.

18. The tissue expander of claim 17, wherein said core comprises upper and lower surfaces and wherein said linking portions are formed as depressions in each of said surfaces.

19. The tissue expander of claim 18, characterized in that said core comprises a regular two dimensional array of segments.

20. The tissue expander of claim 18, characterized in that said core comprises an irregular shaped two dimensional array of segment.

21. The tissue expander of claim 17, characterized in that said core comprises a two dimensional array of segments.

22. The tissue expander of claim 17, characterized in that said linking portions comprise depressions of depth D and width W and wherein said width W decreases as said depth D increases.

23. The tissue expander of claim 17, characterized in that said conformable linking portions comprise compression molded compacted material and are contiguous with said two or more segments.

24. The tissue expander of claim 17, characterized in that said coating comprises a molded coating surrounding said core and molded thereonto.

25. The tissue expander of claim 17, characterized in that said coating includes an outer surface for exposure to moisture and an inner surface in intimate contact with the core and one or more apertures extending from said outer surface to said inner surface such as to allow for the passage of moisture to said core.

26. The tissue expander of claim 25, characterized by further including one or more porous plugs within one or more of said one or more apertures.

27. The tissue expander of claim 25, characterized in that said one or more porous plugs comprise a porous polymer.

28. The tissue expander of claim 25, characterized in that said segments each include upper and lower surfaces and one or more of said one or more apertures are provided at positions which terminate on one or other of said upper or lower surfaces.

29. The tissue expander of claim 17, characterized in that said self-inflating core comprises a hydrogel.

30. The tissue expander of claim 17, characterized in that said coating comprises a water impermeable coating.

31. The tissue expander of claim 30, characterized in that said self-inflating core comprises a compacted material having a central portion of the compacted material having a first higher density HD and a peripheral portion of the compacted material having a second lower density LD less than said first higher density HD, a border between said central portion and said peripheral portion and wherein said coating includes a plurality of first apertures through said coating at positions displaced from said border.

32. The tissue expander of claim 17 characterized in that said segments are each of a different pre-compacted height.

* * * * *